US005817641A

United States Patent [19]
Waldman et al.

[11] Patent Number: 5,817,641
[45] Date of Patent: Oct. 6, 1998

[54] TREATMENT OF ENTEROTOXIGENIC DIARRHEA WITH 2-SUBSTITUTED ADENOSINE DERIVATIVES

[75] Inventors: Scott A. Waldman, Ardmore, Pa.; Scott J. Parkinson, Grimsby, Canada

[73] Assignee: Thomas Jefferson University, Philadelphia, Pa.

[21] Appl. No.: 776,021

[22] PCT Filed: Jul. 21, 1995

[86] PCT No.: PCT/US95/09250

§ 371 Date: Apr. 3, 1997

§ 102(e) Date: Apr. 3, 1997

[87] PCT Pub. No.: WO96/03134

PCT Pub. Date: Feb. 8, 1996

Related U.S. Application Data

[63] Continuation of Ser. No. 278,180, Jul. 21, 1994, abandoned.

[51] Int. Cl.[6] .......................... A61K 31/70; C07H 19/16; C07H 19/167
[52] U.S. Cl. ......................... 514/46; 514/867; 536/27.63
[58] Field of Search ...................... 514/46, 867

[56] References Cited

U.S. PATENT DOCUMENTS

| | | | |
|---|---|---|---|
| 3,845,205 | 10/1974 | Maguire et al. | 514/46 |
| 3,903,073 | 9/1975 | Prasad et al. | 260/211.5 |
| 3,992,531 | 11/1976 | Prasad et al. | 424/180 |
| 4,079,125 | 3/1978 | Sipos | 424/32 |
| 4,701,458 | 10/1987 | Greenberg | 514/867 |
| 4,826,823 | 5/1989 | Cook et al. | 514/46 |
| 4,843,066 | 6/1989 | Yamada et al. | 514/45 |
| 4,956,345 | 9/1990 | Miyasaka et al. | 514/46 |
| 4,968,697 | 11/1990 | Hutchison | 514/46 |
| 4,978,662 | 12/1990 | Nelson et al. | 514/235.8 |
| 4,997,926 | 3/1991 | Haertie et al. | 536/26 |
| 5,034,381 | 7/1991 | Hutchison et al. | 514/26 |
| 5,034,525 | 7/1991 | Montgomery et al. | 536/26 |
| 5,070,877 | 12/1991 | Mohiuddin et al. | 128/653.4 |
| 5,106,837 | 4/1992 | Carson et al. | 514/46 |
| 5,140,015 | 8/1992 | Olsson et al. | 514/46 |
| 5,189,027 | 2/1993 | Miyashita et al. | 514/46 |
| 5,270,304 | 12/1993 | Kogi et al. | 514/46 |
| 5,278,150 | 1/1994 | Olsson et al. | 514/46 |
| 5,280,015 | 1/1994 | Jacobson et al. | 514/46 |
| 5,310,732 | 5/1994 | Carson et al. | 514/46 |

FOREIGN PATENT DOCUMENTS

0423777 A1  4/1991  European Pat. Off. .

OTHER PUBLICATIONS

Boyer et al., "Kinetics of Activation of Phospholipase C by $P_{2Y}$ Purinergic Receptor Agonists and Guanine Nucleotides", *J. Biol. Chem.*, 1989, 264, 884–890.

Bradford, M.M., "A Rapid and Sensitive Method for the Quantitation of Microgram Quantities of Protein Utilizing the Principle of Protein–Dye Binding", *Anal. Biochem.*, 1976, 72, 248–254.

Burger and Lowenstein, "Preparation and Properties of 5'–Nucleotidase from Smooth Muscle of Small Intestine", *J. Biol. Chem.*, 1970, 245, 6274–6280.

Carr et al., "Regulation of Particulate Guanylate Cyclase by *Escherichia Coli* Heat–Stable Enterotoxin: Receptor Binding and Enzyme Kinetics", *Int. J. Biochem.*, 1989, 21, 1211–1215.

Chang et al., "Structural Requirements of ATP for Activation of Basal and Atrial Natriuretic Factor–Stimulated Guanylate Cyclase in Rat Lung Membranes", *Eur. J. Pharmacol.*, 1990, 189, 293–298.

Chinkers et al., "A Membrane Form of Guanylate Cyclase is an Atrial Natriuretic Peptide Receptor", *Nature*, 1989, 338, 78–83.

Chinkers et al., "Adenine Nucleotides Are Required for Activation of Rat Atrial Natriuretic Peptide Receptor/Guanylyl Cyclase Expressed in a Baculovirus System", *J. Biol. Chem.*, 1991, 266, 4088–4093.

Chinkers and Garbers, "The Protein Kinase Domain of the ANP Receptor is Required for Signaling", *Science*, 1989, 245, 1392–1394.

Cohen et al., "Receptors for *Escherichia Coli* Heat Stable Enterotoxin in Human Intestine and in a Human Intestinal Cell Line (Caco–2)", *J. Cell. Physiol.*, 1993, 156, 138–144.

Currie et al., "Guanylin: An Endogenous Activator of Intestinal Guanylate Cyclase", *Proc. Natl. Acad. Sci. USA*, 1992, 89, 947–951.

deSauvage et al., "Primary Structure and Functional Expression of the Human Receptor for *Escherichia Coli* Heat–Stable Enterotoxin", *J. Biol. Chem.*, 1991, 266, 17912–17918.

deSauvage et al., "Characterization of the Recombinant Human Receptor for *Escherichia Coli* Heat Stable Enterotoxin", *J. Biol. Chem.*, 1992, 267, 6479–6482.

Duda et al., "Core Sequence of ATP Regulatory Module in Receptor Guanylate Cyclases", *FEBS Lett.*, 1993, 315, 143–148.

Field et al., "Heat–Stable Enterotoxin of *Escherichia Coli*: In Vitro Effects on Guanylate Cyclase Activity, Cyclic GMP Concentration, and Ion Transport in Small Intestine", *Proc. Natl. Acad. Sci. USA*, 1978, 75, 2800–2804.

Garbers et al., "Kinetic Analysis of Sea Urchin Sperm Guanylate Cyclase", *Biochemistry*, 1974, 13, 4166–4171.

(List continued on next page.)

*Primary Examiner*—Gary L. Kunz
*Attorney, Agent, or Firm*—Woodcock Washburn Kurtz Mackiewicz & Norris, LLP

[57] ABSTRACT

Methods of therapeutically treating individuals suffering from diarrhea comprising the step of administering to such individuals who are suffering from diarrhea, an effective amount of a 2-substituted adenine nucleotide or 2-substituted adenine nucleoside are disclosed. Methods of prophylactically treating individuals to prevent diarrhea comprising the step of administering to individuals who are susceptible to experiencing diarrhea, an effective amount of a 2-substituted adenine nucleotide or 2-substituted adenine nucleoside are disclosed.

45 Claims, No Drawings

OTHER PUBLICATIONS

Garbers, D.L., "Guanylyl Cyclase Receptors and Their Endocrine, Paracrine, and Autocrine Ligands", *Cell,* 1992, 71, 1–4.

Gazzano et al., "Adenine Nucleotide Regulation of Particulate Guanylate Cyclase from Rat Lung", *Biochim. Biophys. Acta,* 1991, 1077, 99–106.

Gazzano et al., "Activation of Particulate Guanylate Cyclase by *Escherichia Coli* Heat–Stable Enterotoxin is Regulated by Adenine Nucleotides", *Infect. Immun.,* 1991, 59, 1552–1557.

Giannella, R.A., "Pathogenesis of Acute Bacterial Diarrheal Disorders", *Annu. Rev. Med.,* 1981, 32, 341–357.

Goraczniak et al., "A Structural Motif that Defines the ATP–Regulatory Module of Guanylate Cyclase in Atrial Natriuretic Factor Signalling", *Biochem. J.,* 1992, 282, 533–537.

Guerrant et al., "Activation of Intestinal Guanylate Cyclase by Heat–Stable Enterotoxin of *Escherichia Coli:* Studies of Tissue Specificity, Potential Receptors, and Intermediates", *J. Infect. Dis.,* 1980, 142, 220–228.

Hill, A.V., "A New Mathematical Treatment of Changes in Ionic Concentration in Muscle and Nerve Under the Action of Electric Currents, with a Theory as to Their Mode of Excitation", *J. Physiol.,* 1910, 40, IV–VII, 190–224.

Hoftsee, B.H.J., "Non–Inverted Versus Inverted Plots in Enzyme Kinetics", *Nature,* 1959, 184, 1296–1298.

Hugues et al., "Identification and Characterization of a New Family of High–Affinity Receptors for *Escherichia Coli* Heat–Stable Enterotoxin in Rat Intestinal Membranes", *Biochem.,* 1991, 30, 10738–10745.

Huott et al., "Mechanism of Action of *Escherichia Coli* Heat Stable Enterotoxin in a Human Colonic Cell Line", *J. Clin. Invest.,* 1988, 82, 514–523.

Ivens et al., "Heterogeneity of Intestinal Receptors for *Escherichia Coli* Heat–Stable Enterotoxin", *Infect. Immun.,* 1990, 58, 1817–1820.

Koller et al., "Selective Activation of the B Natriuretic Peptide Receptor by C–Type Natriuretic Peptide (CNP)", *Science,* 1991, 252, 120–122.

Koller, et al., "Conservation of the Kinaselike Regulatory Domain is Essential for Activation of the Natriuretic Peptide Receptor Guanylyl Cyclases", *Mol. Cell. Biol.,* 1992, 12, 2581–2590.

Li and Goy, "Peptide–Regulated Guanylate Cyclase Pathways in Rat Colon: In Situ Localization of GCA, GCC, and Guanylin mRNA", *Am. J. Physiol.,* 1993, 265, G394–G402.

Lowe et al., "Human Atrial Natriuretic Peptide Receptor Defines a New Paradigm for Second Messenger Signal Transduction", *EMBO J.,* 1989, 8, 1377–1384.

Marala et al., "Dual Regulation of Atrial Natriuretic Factor–Dependent Guanylate Cyclase Activity by ATP", *FEBS Lett.,* 1991, 281, 73–76.

Okajima and Kondo, "Inhibition of Atrial Natriuretic peptide–Induced cGMP Accumulation by Purinergic Agonists in FRTL–5 Thyroid Cells", *J. Biol. Chem.,* 1990, 265, 21741–21748.

Schulz et al., "Cloning and Expression of Guanylin", *J. Biol. Chem.,* 1992, 267, 16019–16021.

Schulz et al., "The Primary Structure of a Plasma Membrane Guanylate Cyclase Demonstrates Diversity within This New Receptor Family", *Cell,* 1989, 58, 1155–1162.

Schulz et al., "Guanylyl Cyclase is a Heat–Stable Enterotoxin Receptor", *Cell,* 1990, 63, 941–948.

Vaandrager et al., "Guanylyl Cyclase C is an N–Linked Glycoprotein Receptor That Accounts for Multiple Heat––Stable Enterotoxin–Binding Proteins in the Intestine", *J. Biol. Chem.,* 1993, 268, 2174–2179.

Vaandrager et al., "Heat–Stable Enterotoxin Activation of Immunopurified Guanylyl Cyclase C", *J. Biol. Chem.,* 1993, 268, 19598–19603.

Vaandrager et al., "Atriopeptins and *Escherichia Coli* Enterotoxin $ST_a$ Have Different Sites of Action in Mammalian Intestine", *Gastroenterology,* 1992, 102, 1161–1169.

Visweswariah et al., "Characterization and Partial Purification of the Human Receptor for the Heat–Stable Enterotoxin", *Eur. J. Biochem.,* 1994, 219, 727–736.

Waldman et al., "A Simple, Sensitive, and Specific Assay for the Heat–Stable Enterotoxin of *Escherichia Coli*", *J. Infect. Dis.,* 1984, 149, 83–89.

Tucker et al., Chemical Abstract No. 102:55990c, "Inhibition by adenosine analogs of opiate withdrawal effects", *NIDA Res. Monogr.,* 1984, 49, 85–91.

TREATMENT OF ENTEROTOXIGENIC DIARRHEA WITH 2-SUBSTITUTED ADENOSINE DERIVATIVES

This application is 371 of PCT/US95/09250 filed Jul. 21, 1995 and a continuation of Ser. No. 08/278,180 filed Jul. 21, 1994.

FIELD OF THE INVENTION

The present invention relates to methods of preventing and treating diarrhea by administering compounds which interfere with the adenine nucleotide-dependent guanylyl cyclase C pathways to an individual at risk of or suffering from diarrhea.

BACKGROUND OF THE INVENTION

Bacteria such as *E. coli* produce a toxin which is resistant to degradation at high temperatures, called the heat-stable enterotoxin (ST). This toxin induces secretion of fluid in the intestine, resulting in diarrhea in individuals infected with these organisms. Indeed, this toxin is a major cause of diarrheal disease in developing countries and a leading cause of morbidity and mortality in the pediatric population worldwide. The toxin induces diarrhea by binding to specific protein receptors in the membranes of intestinal cells which triggers a cascade of biochemical processes eventually leading to fluid secretion into the intestinal lumen. Infectious diarrhea is the fourth leading cause of morbidity and mortality worldwide and the leading cause of morbidity and mortality in the pediatric population. ST-producing bacteria account for the majority of these cases.

Some of the details concerning the cascade of biochemical events in intestinal membranes leading from binding of toxin to the initiation of secretion have been elucidated. Toxin-receptor interaction results in the activation of an enzyme, guanylyl cyclase, which produces a small molecule cyclic GMP. Cyclic GMP directly mediates increased secretion of fluid and electrolytes into the intestine and, consequently, diarrhea.

Receptor guanylyl cyclases are a unique family of proteins whose members contain an extracellular ligand-binding domain directly coupled to a cytoplasmic cyclase catalytic domain (Chinkers et al., (1989) *Nature*, 338, 78–83; Lowe et al., (1989) *EMBO J.*, 8, 1377–1384; Schulz et al., (1989) *Cell*, 58, 1155–1162). Guanylyl cyclase C (GC-C), a recently-described member of this family localized in the brush border of intestinal mucosa cells, is a receptor for the *Escherichia coli* heat-stable enterotoxin (ST; Schulz et al., (1990) *Cell*, 63, 941–948; deSauvage et al., (1991) *J. Biol. Chem.*, 266, 17912–17918). Guanylin, a peptide derived from a precursor protein synthesized in the intestinal epithelium, was recently identified as an endogenous ligand for GC-C (Schulz et al., (1992) *J. Biol. Chem.*, 267, 16019–16021; Currie et al., (1992) *Proc. Natl. Acad. Sci. USA*, 89, 947–951). ST-GC-C interaction is coupled to activation of the intrinsic guanylyl cyclase, increases in intracellular cGMP, and alterations in fluid and electrolyte secretion resulting in secretory diarrhea (Field et al., (1978) *Proc. Natl. Acad. Sci. USA*, 75, 2800–2804; Giannella, R. A., (1981) *Annu. Rev. Med.*, 32, 341–357).

Adenine nucleotides appear to be important in coupling ligand-receptor interaction to enzyme activation in the receptor guanylyl cyclase family. ATP and its analogues potentiate the activation of particulate guanylyl cyclase by ligands such as natriuretic peptides and ST (Gazzano et al., (1991) *Biochim. Biophys. Acta*, 1077, 99–106; Gazzano et al., (1991) *Infect. Immun.*, 59, 1552–1557; Chinkers et al., (1991) *J. Biol. Chem.*, 266, 4088–4093; Duda et al., (1993) *FEBS Lett.*, 315:143–148). Indeed, it has been suggested that activation of particulate guanylyl cyclase by atrial natriuretic peptides (ANP) absolutely requires adenine nucleotides. In addition, ATP activates basal particulate guanylyl cyclase in some studies. It has been suggested that ATP regulates enzyme activity by directly stabilizing the active conformation and inhibiting the desensitization of ligand-induced guanylyl cyclase (Vaandrager et al., (1993) *J. Biol. Chem.*, 268, 2174–2179; Vaandrager et al., (1993) *J. Biol. Chem.*, 268, 19598–19603).

The specific role of ATP in signal transduction mediated by receptor guanylyl cyclases is confounded by the observation that adenine nucleotides inhibit particulate guanylyl cyclase when manganese is used as the substrate cofactor (Marala et al., (1991) *FEBS Lett.*, 281, 73–76). It was suggested previously that this inhibition may reflect competition of ATP with GTP for the substrate binding site on the catalytic domain of guanylyl cyclase. Alternatively, a manganese-specific ATP-binding inhibitory component has been proposed. Although the molecular mechanisms underlying manganese-dependent inhibition by ATP remain to be defined, these studies suggest that ATP may serve both as an activator and inhibitor of receptor-regulated particulate guanylyl cyclase.

The receptor guanylyl cyclases possess a structure similar to receptors of the tyrosine kinase family. Thus, there is an extracellular ligand-binding domain, a single transmembrane domain, a juxtamembrane kinase-like domain important for signal transduction, and a cytoplasmic catalytic domain. The kinase-like domain is an essential regulator of the catalytic guanylyl cyclase domain. Deletion of the kinase-like domain of the ANP receptor (GC-A) results in a constitutively activated guanylyl cyclase, uncoupling ligand binding and adenine nucleotides from guanylyl cyclase activation (Chinkers et al., (1989) *Science*, 245, 1392–1394). These observations suggest that the kinase-like domain of GC-A represses the activity of the catalytic domain, which is relieved by ligand binding. Furthermore, they suggest that the kinase-like domain mediates potentiation of guanylyl cyclase activity by ATP. This suggestion is supported by studies in which membranes from COS-2A cells expressing transfected GC-A cDNA demonstrated increased specific ATP binding compared to membranes from cells expressing GC-A kinase-like domain-deficient mutants (Goraczniak et al., (1992) *Biochem. J.*, 282, 533–537).

There are currently no pharmaceutical agents which can terminate the signaling induced by ST leading to intestinal secretion and diarrhea. Indeed, the current approach to treating secretory diarrhea is fluid and electrolyte replacement, antibiotics, and anti-motility agents such as opiate derivatives. There is a need for compounds which directly interrupt of the signaling process leading from toxin exposure to intestinal secretion. There is a need for compounds whose effects are relatively specific for ST-stimulated guanylyl cyclase and should not effect other members of this enzyme family. There is a need for an effective methods of treating and preventing GC-C-mediated diarrhea.

SUMMARY OF THE INVENTION

The present invention relates to methods of therapeutically treating individuals suffering from diarrhea comprising the step of administering to such individuals who are suffering from diarrhea, particularly infectious diarrhea, an effective amount of a 2-substituted adenine nucleotide or 2-substituted adenine nucleoside.

The present invention relates to methods of prophylactically treating individuals to prevent diarrhea comprising the step of administering to individuals who are susceptible to experiencing diarrhea, particularly infectious diarrhea, an effective amount of a 2-substituted adenine nucleotide or 2-substituted adenine nucleoside.

The 2-substituted adenine nucleotides and 2-substituted adenine nucleosides useful in the methods in the present invention include those having the formula:

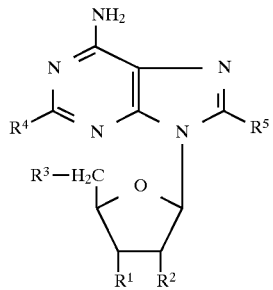

wherein:

$R^1$ is OH or H;

$R^2$ is OH or H;

$R^3$ is OH, $PO_4H_2$, $P_2O_7H_3$, $P_3O_{10}H_4$ or $P_4O_{13}H_5$;

$R^4$ is halogen, $C_1$–$C_4$ alkyl, $C_1$–$C_4$ alkoxyl, $C_1$–$C_4$ alkylthiol; and, $R^5$ is H, Cl or Br;

or a pharmaceutically acceptable salt thereof.

DETAILED DESCRIPTION OF THE INVENTION

As used herein, guanylyl cyclase C-mediated diarrhea or GC-C-mediated diarrhea is meant to refer to diarrhea which is associated with guanylyl cyclase C (GC-C) enzyme activity. An example of GC-C-mediated diarrhea is infectious diarrhea which is brought about by GC-C enzyme activation when the E. coli heat stable toxin (ST) binds to receptors on cells within the colon of an individual. Infectious diarrhea is also referred to herein as E. coli heat stable toxin induced diarrhea.

This application is related to U.S. Ser. No. 08/278,180, which is incorporated herein by reference. We have determined that there is a regulatory pathway which inhibits guanylyl cyclase activity that has been stimulated by ST. This pathway is triggered specifically by analogs of ATP that possess a modification of their structure in the 2' position of the purine ring. Compounds of the invention specifically and almost completely inhibit ST-activated guanylyl cyclase in cell-free membrane preparations of intestinal cells. In addition, these compounds inhibit the accumulation of cyclic GMP stimulated by ST in intact intestinal cells made permeable to low molecular weight compounds (permeabilized cells). These agents appear to be selective for guanylyl cyclase coupled to ST, since they demonstrated a decreased ability to alter the activity of other guanylyl cyclases coupled to different hormones. Thus, according to the present invention, 2'-substituted analogs specifically interrupt the signaling cascade mediating ST activation of guanylyl cyclase, and consequently the ability of these compounds to prevent diarrhea induced by this toxin. 2-substituted nucleotides are relatively inexpensive and should be effective in an oral formulation. Furthermore, given their characteristic inhibition of guanylyl cyclase, these agents should be rapidly effective upon administration but with a rapid half-life of effect once administration is terminated.

Accordingly, the present invention relates to a method of negatively regulating guanylyl cyclase C (GC-C) enzyme activity by activating an inhibitory pathway. According to the present invention, GC-C enzyme activity is inhibited by contacting cells that have active GC-C enzyme with an effective amount of a 2-substituted adenine nucleotide or nucleoside analog, or a pharmaceutically acceptable salt thereof. GC-C inhibitors are useful to prevent or treat GC-C-mediated diarrhea. The present invention relates to a method of preventing an individual from suffering from GC-C-mediated diarrhea, such as infectious diarrhea, comprising the step of administering to such an individual, an amount of a 2-substituted adenine nucleotide or nucleoside analog, or a pharmaceutically acceptable salt thereof to inhibit GC-C activity. The present invention relates to a method of treating an individual suffering from GC-C-mediated diarrhea, such as infectious diarrhea, comprising the step of administering to such an individual, an amount of a 2-substituted adenine nucleotide or nucleoside analog, or a pharmaceutically acceptable salt thereof to inhibit GC-C activity.

The method of the present invention comprises inhibiting GC-C activity by contacting cells that have active GC-C with an effective amount of a 2-substituted adenine nucleotide or nucleoside analog, or a pharmaceutically acceptable salt thereof. 2-substituted adenine nucleotide and nucleoside analogs have been discovered to be agonists in an inhibitory pathway which negatively regulates the activity of GC-C. Exposure of cells in vitro to 2' substituted adenine nucleotide or nucleoside analogs has resulted in the inhibition of GC-C activity. Inhibition of GC-C activity in cells impedes the pathway associated with GC-C-mediated diarrhea.

The method that is the present invention is useful in the prevention and treatment of conditions associated with active GC-C; specifically GC-C-mediated diarrhea such as infectious diarrhea. Accordingly, the present invention relates to a method of preventing GC-C-mediated diarrhea in or treating a individual suffering from GC-C-mediated diarrhea. The present invention relates to a method of preventing infectious in an a individual susceptible to infectious diarrhea. The present invention relates to a method of treating an individual suffering from infectious diarrhea. The individual is preferably a mammal, more preferably a human. In some embodiments, the individual may be a canine, feline or equine species.

The identification of an individual suspected of suffering from GC-C-mediated diarrhea such as infectious diarrhea is routine and can be performed by those having ordinary skill in the art. Infectious diarrrhea can be identified routinely. In addition to being useful to treating individuals suspected of suffering from GC-C-mediated diarrhea, the present invention is useful prophylactically to prevent the incidence of GC-C-mediated diarrhea in individuals at risk of contracting the condition. For example, travellers and those living in situations for which the are unaccustomed may be at risk. Those having ordinary skill in the art can readily identify conditions which place an individual at risk of contracting GC-C-mediated infectious diarrhea.

According to the invention, opposing pathways by which adenine nucleotides and nucleosides regulate ST-activated particulate guanylyl cyclase in intestinal membranes have been defined and characterized. According to the invention, adenine nucleotide and nucleoside analogues which behave as specific agonists of the activating or inhibitory pathways have been identified. The inhibitory pathway reflects a novel regulatory mechanism. The structural attributes of adenine nucleotides important for determining agonist specificities have been defined.

Various amounts of test compound are used to determine the level of inhibitory activity that the particular test compound possesses. Assay conditions such as pH, salt and cofactor conditions are maintained similar to physiological levels in order to duplicate in vivo conditions.

In some preferred embodiments, the method that is the invention is a method of treating an individual suspected of suffering from GC-C mediated diarrhea comprising the step of:

administering to said individual, an effective amount of a 2-substituted adenine nucleotide or 2-substituted adenine nucleoside compound.

In some preferred embodiments, the method that is the invention is a method of preventing GC-C mediated diarrhea in an individual comprising the step of:

administering to said individual, an effective amount of a 2-substituted adenine nucleotide or 2-substituted adenine nucleoside compound.

Compounds useful in the methods of the present invention can be expressed by the formula:

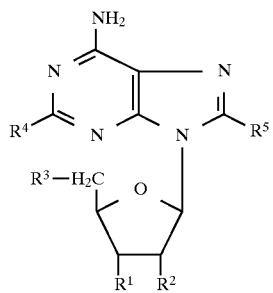

wherein:

$R^1$ is OH or H;

$R^2$ is OH or H;

$R^3$ is OH, $PO_4H_2$, $P_2O_7H_3$, $P_3O_{10}H_4$ or $P_4O_{13}H_5$;

$R^4$ is halogen, $C_1$–$C_4$ alkyl, $C_1$–$C_4$ alkoxyl, $C_1$–$C_4$ alkylthiol; and, $R^5$ is H, Cl or Br.

In addition, pharmaceutically acceptable salts of these compounds may be used in the method that is the present invention.

Compounds useful in methods according to the present invention can have at position $R^1$ either OH or H. According to some preferred embodiments, $R^1$ is preferably OH.

Compounds useful in methods according to the present invention can have at position $R^2$ either OH or H. According to some preferred embodiments, $R^2$ is preferably OH.

According to some embodiments, the compound used according to the present invention is a ribonucleotide or a ribonucleoside. In such cases, both $R^1$ and $R^2$ are OH.

According to some embodiments, the compound used according to the present invention is a deoxyribonucleotide or a deoxyribonucleoside. In such cases, one of either $R^1$ or $R^2$ is H and the other is OH.

According to some embodiments, the compound used according to the present invention is a dideoxyribonucleotide or a dideoxyribonucleoside. In such cases, both $R^1$ and $R^2$ are H.

Compounds useful in methods according to the present invention can have at position $R^3$ either OH, $PO_4H_2$, $P_2O_7H_3$, $P_3O_{10}H_4$ or $P_4O_{13}H_5$.

According to some embodiments, the compound used according to the present invention is a nucleoside. In such cases, $R^3$ is OH.

According to some embodiments, the compound used according to the present invention is a monophosphate nucleotide. In such cases, $R^3$ is $PO_4H_2$. In some embodiments, the compounds used in the method that is the present invention is a salt and $R^3$, which is $PO_4H_2$, exists as $PO_4H^-$.

According to some embodiments, the compound used according to the present invention is a diphosphate nucleotide. In such cases, $R^3$ is $P_2O_7H_3$. In some embodiments, the compounds used in the method that is the present invention is a salt and $R^3$, which is $P_2O_7H_3$, exists as $P_2O_7H^{2-}$.

According to some embodiments, the compound used according to the present invention is a triphosphate nucleotide. In such cases, $R^3$ is $P_3O_{10}H_4$. In some embodiments, the compounds used in the method that is the present invention is a salt and $R^3$, which is $P_3O_{10}H_4$, exists as is $P_3O_{10}H^{3-}$.

According to some embodiments, the compound used according to the present invention is a tetraphosphate nucleotide. In such cases, $R^3$ is $P_4O_{13}H_5$. In some embodiments, the compounds used in the method that is the present invention is a salt and $R^3$, which is $P_4O_{13}H_5$, exists as is $P_4O_{13}H_4^-$.

Compounds useful in methods according to the present invention can have at position $R^4$: a halogen such as F, Cl, Br, I or At; a $C_1$–$C_4$ alkyl such as methyl, ethyl, propyl or butyl; a $C_1$–$C_4$ alkyloxyl such as methyoxy, ethoxy, propyloxy or butyloxy; or a $C_1$–$C_4$ alkylthiol such as methylthio, ethylthio, propylthio or butylthio.

Compounds useful in methods according to the present invention can have at position $R^5$: H, Cl or Br. In some embodiments, the molecule is substituted at position 8 with Br or Cl in order to facilitate uptake of the compound by the cells.

According to some embodiments of the invention, $R^1$ is OH; $R^2$ is OH; $R^3$ is OH, $PO_4H_2$, $P_2O_7H_3$ or $P_3O_{10}H_4$; $R^4$ is Cl, $C_1$–$C_2$ alkyl, $C_1$–$C_2$ alkoxyl, $C_1$–$C_2$ alkylthiol; and, $R^5$ is H or Br.

According to some embodiments of the invention, $R^1$ is OH; $R^2$ is OH; $R^3$ is OH, $PO_4H_2$, $P_2O_7H_3$ or $P_3O_{10}H_4$; $R^4$ is Cl, methyl, methoxy or methylthiol; and, $R^5$ is H or Br.

According to some embodiments of the invention, $R^1$ is OH; $R^2$ is OH; $R^3$ is OH, $PO_4H_2$, $P_2O_7H_3$ or $P_3O_{10}H_4$; $R^4$ is Cl; and, $R^5$ is H or a salt thereof.

According to some embodiments of the invention, $R^1$ is OH; $R^2$ is OH; $R^3$ is OH, $PO_4H_2$, $P_2O_7H_3$ or $P_3O_{10}H_4$; $R^4$ is Cl; and $R^5$ is H; and $R^3$ is OH.

According to some embodiments of the invention, $R^1$ is OH; $R^2$ is OH; $R^3$ is OH, $PO_4H_2$, $P_2O_7H_3$ or $P_3O_{10}H_4$; $R^4$ is Cl; $R^5$ is H; and $R^3$ is $PO_4H_2$ or $PO_4H^-$.

According to some embodiments of the invention, $R^1$ is OH; $R^2$ is OH; $R^3$ is OH, $PO_4H_2$, $P_2O_7H_3$ or $P_3O_{10}H_4$; $R^4$ is Cl; $R^5$ is H; and $R^3$ is $P_2O_7H_3$ or $P_2O_7H^{2-}$.

According to some embodiments of the invention, $R^1$ is OH; $R^2$ is OH; $R^3$ is OH, $PO_4H_2$, $P_2O_7H_3$ or $P_3O_{10}H_4$; $R^4$ is Cl; $R^5$ is H; and $R^3$ is $P_3O_{10}H_4$ or $P_3O_{10}H^{3-}$.

According to some embodiments of the invention, $R^1$ is OH; $R^2$ is OH; $R^3$ is OH, $PO_4H_2$, $P_2O_7H_3$ or $P_3O_{10}H_4$; $R^4$ is methylthiol; and, $R^5$ is H or a salt thereof.

According to some embodiments of the invention, $R^1$ is OH; $R^2$ is OH; $R^3$ is OH, $PO_4H_2$, $P_2O_7H_3$ or $P_3O_{10}H_4$; $R^4$ is methylthiol; $R^5$ is H; and $R^3$ is OH.

According to some embodiments of the invention, $R^1$ is OH; $R^2$ is OH; $R^3$ is OH, $PO_4H_2$, $P_2O_7H_3$ or $P_3O_{10}H_4$; $R^4$ is methythiol; $R^5$ is H; and $R^3$ is $PO_4H_2$ or $PO_4H^-$.

According to some embodiments of the invention, $R^1$ is OH; $R^2$ is OH; $R^3$ is OH, $PO_4H_2$, $P_2O_7H_3$ or $P_3O_{10}H_4$; $R^4$ is methylthiol; $R^5$ is H; and $R^3$ is $P_2O_7H_3$ or $P_2O_7H^{2-}$.

According to some embodiments of the invention, $R^1$ is OH; $R^2$ is OH; $R^3$ is OH, $PO_4H_2$, $P_2O_7H_3$ or $P_3O_{10}H_4$; $R^4$ is methylthiol; $R^5$ is H; and $R^3$ is $P_3O_{10}H_4$ or $P_3O_{10}H^{3-}$.

It is also contemplated that compounds useful in the method of the present invention include those in which $R^3$ is carboxyethylphenethylamine, chloro-$N^6$-cyclopentyl, phenylamine or $N^6$-phenylisopropyl. Other contemplated substitutions include other carboxy-amino groups such as carboxymethylphenethylamino; other cyclic aliphatics and aromatics such as chloro-$N^6$-cyclobutyl, chloro-$N^6$-cyclohexyl or chloro-$N^6$-phenyl; and substituted phenylamine groups such as methylphenylamine, ethylephenylamine, chlorophenylamine, and $N^6$-phenylpropyl. Other contemplated substitutions include $C_1$–$C_{20}$ alkyl, $C_3$–$C_6$ cycloalkyl, $C_3$–$C_6$ aryl, $C_2$–$C_{20}$ alkenyl, $C_2$–$C_{20}$ alkynyl, $C_4$–$C_{20}$alkylaryl, $C_4$–$C_{20}$ arylalkyl, halogen, nitro, amino, $C_1$–$C_{20}$ acylamino, hydroxy, $C_1$–$C_{20}$ alkoxycarbonyl, cyano, trihalomethyl, carboxyl, $C_1$–$C_{20}$ alkoxy, $C_1$–$C_{20}$ alkylthio, or $C_3$–$C_6$ arylthio.

Pharmaceutically acceptable salts of these compounds may be used in practicing the method that is the present invention. Pharmaceutical compositions containing the compounds or salts may also be used in practicing the method that is the present invention. Pharmaceutically acceptable salts useful in the method of that is the invention include sodium, potassium, calcium, zinc, lithium, magnesium, aluminum, diethanolamine, tromethamine, ethylenediamine, meglumine, hydrochloric, hydrobromic or acetic acid.

Compounds of the present invention are commercially available from many sources including Research Biochemical International, Natick, Mass. Compounds used in the present invention may also be synthesized from readily available starting materials by standard techniques following the basic synthesis such as those for example which are set out in U.S. Pat. No. 5,310,732, U.S. Pat. No. 5,280,015, U.S. Pat. No. 5,278,150, U.S. Pat. No. 5,270,304, U.S. Pat. No. 5,189,027, U.S. Pat. No. 5,140,015, U.S. Pat. No. 5,106,837, U.S. Pat. No. 5,034,518, U.S. Pat. No. 5,034,381, U.S. Pat. No. 4,997,926, U.S. Pat. No. 4,968,697, U.S. Pat. No. 4,956,345, U.S. Pat. Nos. 4,843,066, and 3,903,073, the disclosures of which are each incorporated herein by reference. It is contemplated that the compounds that are disclosed in the references are also useful for practicing the methods of the present invention as taught herein and that such compounds may be used according to the present invention in the methods described herein.

The present invention relates to a method of using 2-substituted adenine nucleotides and nucleosides to inhibit the activity of GC-C in cells. The range of amounts of inhibitory compound that a cell can be exposed to that is effective for inhibiting GC-C activity can be determined by one having ordinary skill in the art.

By inhibiting GC-C activity, the method that is the present invention is useful in the treatment of GC-C-mediated diarrhea. Effective amounts of compounds used in the method that is the present invention can be formulated as pharmaceutical preparations and administered to individuals who are suspected of suffering from or being susceptible to GC-C mediated diarrhea, in order to counter the biochemical pathway which leads to the condition at the cellular level.

Treatment of GC-C-mediated diarrhea can be performed by administration of effective amounts of a pharmaceutical preparation of 2-substituted adenine nucleotides and nucleosides to inhibit GC-C. Compounds can be formulated for human and animal prophylactic and therapeutic applications by those having ordinary skill in the art. The dosage range of a compound to be administered to mammals, particularly humans, to be effective in the treatment or prevention of GC-C mediated diarrhea can be determined by those having ordinary skill in the art.

Pharmaceutical preparations incorporating compounds used in the method that is the invention can be used to block GC-C activity related to the biochemical pathway which results in diarrhea by administration of effective amounts of pharmaceutical preparation that comprise compounds disclosed herein. The compounds used in the method that is the invention can be formulated for human and animal prophylactic and therapeutic applications by those having ordinary skill in the art. The range of amounts of a compound to be administered to mammals, particularly humans, to be effective in treating or preventing GC-C-mediated diarrhea can be determined by those having ordinary skill in the art.

The mode of administration of compounds and pharmaceutical compositions according to the method that is the invention includes any means that produces contact of the active ingredient with the agent's site of action in the body of a mammal, that is in the cells of the colon. These modes of administration include but not limited to oral, topical, hypodermal, intravenous, intraanally, intramuscular and intraparenteral methods of administration. The preferred route of administration is orally.

In practicing the method that is the invention, the compounds may be administered singly or in combination with other compounds useful for treating or preventing diarrhea. In the method that is the invention, the compounds are preferably administered with a pharmaceutically acceptable carrier selected on the basis of the selected route of administration and standard pharmaceutical practice.

The method may include administration of compounds to mammals, preferably humans, in therapeutically effective amounts which are effective to inhibit GC-C. The dosage administered in any particular instance will depend upon factors such as the pharmacodynamic characteristics of the compound of the invention, its mode and route of administration; age, health, and weight of the recipient; nature and extent of symptoms; kind of concurrent treatment, frequency of treatment, and the effect desired.

It is contemplated that the daily dosage of a compound used in the method that is the invention will be in the range of from about 1 μg to about 10 grams per day. In some preferred embodiments, the daily dosage compound will be in the range of from about 10 mg to about 1 gram per day. In some preferred embodiments, the daily dosage compound will be in the range of from about 100 mg to about 500 mg per day. It is contemplated that the daily dosage of a compound used in the method that is the invention will be in the range of from about 1 μg to about 100 mg per kg of body weight, in some embodiments, from about 1 μg to about 40 mg per kg body weight; in some embodiments from about 10 μg to about 20 mg per kg per day, and in some embodiments 10 μg to about 1 mg per kg per day.

Pharmaceutical compositions may be administered in a single dosage, divided dosages or in sustained release. In some preferred embodiments, the compound will be administered in multiple doses per day. In some preferred embodiments, the compound will be administered in 3–4 doses per day.

Persons of ordinary skill will be able to determine dosage forms and amounts with only routine experimentation based upon the considerations of this invention. Isomers of the compounds and pharmaceutical compositions, particularly optically active stereoisomers, are also within the scope of the present invention.

The method of administering compounds include administration as a pharmaceutical composition orally in solid dosage forms, such as capsules, tablets, and powders, or in liquid dosage forms, such as elixirs, syrups, and suspensions. The compounds may also be administered parenterally in sterile liquid dosage forms or topically in a carrier. The compounds may be formulated into dosage forms according to standard practices in the field of pharmaceutical preparations. See Remington's Pharmaceutical Sciences, A. Osol, Mack Publishing Company, Easton, Pa.

Compounds may be mixed with powdered carriers, such as lactose, sucrose, mannitol, starch, cellulose derivatives, magnesium stearate, and stearic acid for insertion into gelatin capsules, or for forming into tablets. Both tablets and capsules may be manufactured as sustained release products for continuous release of medication over a period of hours. Compressed tablets can be sugar or film coated to mask any unpleasant taste and protect the tablet from the atmosphere or enteric coated for selective disintegration in the gastrointestinal tract. In some preferred embodiments, compounds are delivered orally and are coated with an enteric coating which makes the compounds available upon passing through the stomach and entering the intestinal tract, preferably upon entering the large intestine. U.S. Pat. No. 4,079,125, which is incorporated herein by reference, teaches enteric coating which may be used to prepare enteric coated 2 substituted adenine nucleotides and nucleotides useful in the methods of the invention.

Liquid dosage forms for oral administration may contain coloring and flavoring to increase patient acceptance, in addition to a pharmaceutically acceptable diluent such as water, buffer or saline solution.

For parenteral administration, a compound may be mixed with a suitable carrier or diluent such as water, a oil, saline solution, aqueous dextrose (glucose), and related sugar solutions, and glycols such as propylene glycol or polyethylene glycols. Solutions for parenteral administration contain preferably a water soluble salt of the compound. Stabilizing agents, antioxidizing agents and preservatives may also be added. Suitable antioxidizing agents include sodium bisulfite, sodium sulfite, and ascorbic acid, citric acid and its salts, and sodium EDTA. Suitable preservatives include benzalkonium chloride, methyl- or propyl-paraben, and chlorbutanol.

The following non-limiting Examples illustrate the methods useful for studying compounds which can be used in the methods of the invention and further provides a listing of some preferred compounds.

EXAMPLES

Example 1

SUMMARY

Opposing adenine nucleotide-dependent pathways regulating guanylyl cyclase C (GC-C) in rat intestinal membranes have been identified and characterized. ATP-analogues substituted in the 2-position were potent inhibitors of basal and E. coli heat-stable enterotoxin (ST)-stimulated particulate guanylyl cyclase, independent of the metal cation cofactor present. Indeed, all adenine nucleotides tested inhibited particulate guanylyl cyclase when manganese served as the cation cofactor except AMPS, which had no effect on enzyme activity in the presence of manganese, but retained the ability to potentiate activation of guanylyl cyclase by ST when magnesium was present. Adenine nucleotide inhibition of GC-C enzyme activity was associated with large changes in $V_{max}$ but only small changes in the $S_{0.5}$ suggesting a non-competitive mechanism. Also, this inhibition was associated with a concentration-dependent decrease in the Hill coefficient and a concomitant shift from positive to negative cooperativity of the enzyme when manganese served as the cation cofactor. These data support the existence of a non-competitive regulatory mechanism mediating adenine nucleotide-dependent inhibition of GC-C. Adenine nucleotides also potentiated the activation of particulate guanylyl cyclase by ST in intestinal membranes. Potentiation of enzyme activity was preferentially observed in the presence of magnesium, using nucleotides which were not substituted in the 2-position of the adenine ring and possessed a free thiol group on the terminal phosphate. The potentiating and inhibitory pathways regulating GC-C enzyme activity were separate and distinct. A specific agonist of the inhibitory pathway (2ClATP), was without effect on the potency of a specific agonist of the activating pathway, (AMPS), to regulate GC-C. Similarly, AMPS was without effect on the potency of 2ClATP to inhibit guanylyl cyclase. These data suggest that adenine nucleotide-dependent activation and inhibition of GC-C are mediated by separate and independent sites which may modulate the second messenger response to GC-C to ST.

MATERIALS AND METHODS

Preparation of Rat Intestinal Membranes

Membranes were prepared from rat intestinal mucosa cells as described previously (Gazzano et al., (1991) Infect. Immun., 59, 1552–1557, which is incorporated herein by reference). Briefly, Sprague-Dawley rats were sacrificed, small intestine removed and rinsed in ice-cold 0.9% NaCl. All procedures were conducted at 4° C. The mucosal layer was scraped from the intestine and homogenized in 50 mM Tris-HCl (pH 7.6) containing 1 mM dithiothreitol, 1 mM EDTA and 1 mM phenylmethylsulfonyl fluoride, (TED) supplemented with 0.25M sucrose (TEDS). Homogenates were centrifuged at 100,000×g for 60 minutes and the resulting pellet was sequentially washed in (i) TED supplemented with 0.5M KCl, (ii) TED:TEDS (1:1) and (iii) TED. The final pellet was homogenized in TED at a protein concentration of 5–10 mg/mL and aliquots were stored at −70° C. These membranes possessed particulate guanylyl cyclase activity that was stimulated by ST which is characteristic of GC-C. In contrast, these membranes were devoid of guanylyl cyclase activity stimulated by ANP ($10^{-5}$M) or C-type natriuretic peptide (CNP; $10^{-5}$M) in the presence or absence of 1 mM ATP, demonstrating the absence of GC-A and GC-B in these preparations (Koller et al., (1991) Science, 252, 120–123; Garbers, D. L., (1992) Cell, 71, 1–4; Vaandrager et al., (1992) Gastroenterology, 102, 1161–1169; Li et al., (1993) Am. J. Physiol., 265, G394–G402).

Guanylyl Cyclase Assay

Guanylyl cyclase activity was assayed as described previously (Waldman et al., (1984) J. Infect. Dis., 149, 83–89, which is incorporated herein by reference). Membranes were incubated at 37° C. in a final volume of 100 μl in the presence of 50 mM Tris-HCl (pH 7.6) containing 10 mM theophylline, 7.5 mM creatine phosphate/20 μM creatine phosphokinase (160 U/mg of protein), GTP, manganese or magnesium cofactor (2 mM in excess of nucleotide) and ST and/or adenine nucleotide where indicated. Reactions were initiated by addition of membrane, incubated 5 minutes and terminated by adding 400 µl of 50 mM sodium acetate (pH 4.0) and boiling for 5 minutes. Following acetylation, samples were diluted with 50 mM NaAc containing 20 mM CaCl$_2$. Generated cGMP was quantified by radioimmunoassay as described previously (Waldman et al., (1984) *J. Infect. Dis.*, 149, 83–89). Radioimmunoassays were performed in triplicate, enzyme reactions were performed in duplicate, and results are representative of at least 3 experiments. Enzyme activity was linear with respect to protein concentration and time for all experiments.

ST Receptor Binding Assay

ST binding was quantified as described previously (Hugues et al., (1991) *Biochemistry*, 30, 10738–10745, which is incorporated herein by reference). Briefly, 10–20 µg of protein was incubated in 50 mM Tris-HCl (pH 7.6) containing 1 mM EDTA, 150 mM KCl, 0.1% bacitracin and 0.67 mM cystamine (binding buffer), in the presence of [$^{125}$I]-ST ($10^{-9}$M; 1000 Ci/mmol). Parallel incubations contained excess ($10^{-6}$M) unlabeled ST to quantify non-specific binding. Reaction mixtures were incubated for 40 minutes at 37° C. and bound [$^{125}$I]-ST was separated from free ligand by vacuum filtration through Whatman (GF/B glass fiber filters pretreated with 0.3% polyethyleneimine. Filters were washed with 10 ml of 20 mM phosphate-buffered saline (pH 7.2) containing 1 mM EDTA. Radioactivity which remained on the filter was quantified in a Packard γ-counter. Specific binding was determined by subtracting non-specific binding from the total [$^{125}$I]-ST bound in the absence of unlabeled ligand. Non-specific binding was routinely less than 20% of total binding.

Miscellaneous

Protein concentration was measured by the method of Bradford (Bio-Rad) using bovine serum albumin as standard (Bradford, M. M., (1976) *Anal. Biochem.*, 72, 248–254). All assays were performed in duplicate and data are representative of at least 3 experiments. Values reported for the $S_{0.5}$ and $V_{max}$ are equivalent to the concentration of substrate yielding half-maximum guanylyl cyclase activity and the maximum velocity of the enzyme activity, respectively. All nucleotides were obtained from Sigma, except 2-chloroadenosine 5'-triphosphate (2ClATP) which were from Research Biochemicals Incorporated (Natick, Mass.).

RESULTS

The effects of adenine nucleotides on basal and ST-activated particulate guanylyl cyclase in intestinal membranes were examined using magnesium as the cation cofactor. In the presence of maximally-activating concentrations of ST (1 µM), adenine nucleotides which were not substituted at the 2-position activated guanylyl cyclase with the following rank order of potency: adenosine 5'-O-(3-thiotriphosphate) (ATPγS)>ATP>adenosine 5'-O-thiomonophosphate (AMPS). Guanylyl cyclase was maximally activated 2- to 3-fold by ATPγS in the presence of ST in a concentration-dependent fashion, as demonstrated previously (Gazzano et al., (1991) *Infect. Immun.*, 59, 1552–1557). ATP also activated guanylyl cyclase in a concentration-dependent manner but with a lower efficacy than ATPγS. Also, AMPS potentiated guanylyl cyclase activation by ST in a concentration-dependent fashion in rat intestinal membranes with a similar efficacy to ATP. This is similar to its effect on basal guanylyl cyclase activity observed in membranes prepared from rat lung (Gazzano et al., (1991) *Biochim. Biophys. Acta*, 1077, 99–106).

In contrast, under identical incubation conditions, the 2-substituted adenine nucleotide analogues 2MeSATP and 2ClATP inhibited guanylyl cyclase activity. Enzyme inhibition by 2-substituted ATP analogues was independent of the inclusion of ST in incubations and $K_i$ values for these analogues were not significantly different in the presence of absence of this ligand. Inhibition by the 2-substituted analogues was concentration-dependent and maximum inhibition by these nucleotides was >95%. These data suggest that substitution at the 2-position of the adenine ring is important for inhibition of guanylyl cyclase by adenine nucleotides.

Using manganese as the substrate cofactor, adenine nucleotide analogues inhibited guanylyl cyclase in a concentration-dependent fashion with the following rank order of potency: 2ClATP>2MeSATP>ATP=α,β-methylene adenosine 5'-triphosphate (AMPCPP)-βγ-methylene adenosine 5'-triphosphate (AMPPCP)>ATPγS=adenosine 5'-O-(2-thiodiphosphate) (ADPβS). In close agreement with results obtained with magnesium as the substrate cofactor, >95% of the guanylyl cyclase activity was inhibited by the 2-substituted ATP analogues. Of significance, AMPS and 2ClAdo did not significantly inhibit guanylyl cyclase suggesting that the β and γ terminal phosphates are critical structural features for expression of adenine nucleotide-dependent inhibition of this enzyme. In the presence of manganese, the 2-substituted ATP analogues are the most potent inhibitors of guanylyl cyclase. Using magnesium as the cation cofactor, 2ClATP and 2MeSATP inhibit guanylyl cyclase without potentiating activation of this enzyme by peptide ligand, in contrast to other ATP analogues. These data suggest that substitution at the 2-position of the adenine ring is a structural determinant important for adenine nucleotide-dependent inhibition, and also precludes adenine nucleotide-dependent activation, of particulate guanylyl cyclase.

Previously, adenine nucleotides were demonstrated to inhibit specific [$^{125}$I]-ST binding to rat intestinal mucosa membranes. The possibility that 2-substituted analogues of ATP inhibited ST activation of guanylyl cyclase by preventing binding of this toxin to receptors was examined. Specific binding of [125I]-ST to the intestinal membranes was unchanged by maximally inhibitory concentrations (1 mM) of 2ClATP in the presence or absence of GTP and magnesium. These data suggest the 2ClATP did not inhibit the enzyme by preventing ligand-receptor interaction. This suggestion is supported by the observation that 2ClATP and 2MeSATP inhibit guanylyl cyclase in the presence or absence of ST.

Results suggest that adenine nucleotides can be grouped in three categories: those which (1) only potentiate guanylyl cyclase activation (AMPS), (2) potentiate activation of the enzyme in the presence of magnesium but inhibit guanylyl cyclase in the presence of manganese (ATPγS, ATP), and (3) only inhibit guanylyl cyclase when either metal is utilized as the cation cofactor (2MeSATP, 2ClATP). This classification suggests that adenine nucleotide-dependent inhibition and activation do no share a common active site since these pathways demonstrate different structural requirements for their respective effects. The activating pathway is stimulated by AMPS suggesting that the β and γ phosphate groups are not absolutely required for this function. However, these terminal phosphates are absolutely required for initiation of the inhibitory pathway. Furthermore, substitution at the 2-position of the adenine ring appears to prevent initiation by ATP analogues of the activating pathway, since the fold activation of guanylyl cyclase by ST is not affected by 2ClATP or 2MeSATP. In contrast, substitution at the 2-position of the adenine ring markedly improves the potency and efficacy of ATP analogues to inhibit particulate guanylyl cyclase utilizing either divalent cation as the cofactor. These date define conditions and specific agonists which can be used to further investigate adenine nucleotide-dependent activation and inhibition of particulate guanylyl cyclase.

The effects of adenine nucleotide-dependent inhibition on the kinetic characteristics of particulate guanylyl cyclase in intestinal membranes were examined. When manganese is employed as the substrate cofactor, all triphosphate analogues of ATP studied inhibited guanylyl cyclase, suggesting that the inhibitory pathway is expressed selectively in the presence of this divalent cation. Similarly, the 2-substituted adenine nucleotides selectively activated the inhibitory pathway when either divalent cation was used as the substrate cofactor. Thus, guanylyl cyclase kinetics were examined in the presence and absence of 2MeSATP utilizing manganese as the cation cofactor. Guanylyl cyclase activity increased in a concentration-dependent and saturable fashion with respect to manganese-GTP. 2MeSATP (1 mM) decreased the $V_{max}$ of guanylyl cyclase in a concentration-dependent fashion, with a maximum inhibition of >90%, while having only a small effect on the $S_{0.5}$. ATP (1 mM) exhibited similar inhibitory characteristics in the presence of manganese, decreasing the $V_{max}$ 80% while increasing $S_{0.5}$ from 0.08 to 0.25 mM.

The decrease in $V_{max}$ produced by 2MeSATP suggests that this nucleotide inhibits particulate guanylyl cyclase in a non-competitive competitive fashion. This hypothesis was further examined by determining whether potency of 2MeSATP to inhibit this enzyme was decreased by increasing the concentration of metal-nucleotide substrate, as would be expected for competitive inhibition. Indeed, no significant difference in the potency of 2MeSATP to inhibit guanylyl cyclase was observed in the presence of 20 μM or 1000 μM GTP ($K_i$=0.39±0.26 mM and 0.28±0.18 mM, respectively). These data further support the suggestion that inhibition of guanylyl cyclase by adenine nucleotides occurs by a non-competitive mechanism.

Also, a non-competitive mechanism for inhibition of guanylyl cyclase by adenine nucleotides was suggested when enzyme kinetics were analyzed utilizing magnesium as the substrate cofactor. Guanylyl cyclase activity increased in a concentration-dependent and saturable fashion with respect to magnesium-GTP. ST increased the $V_{max}$ without significantly changing the $S_{0.5}$, as demonstrated previously. 2MeSATP (1 mM) lowered the $V_{max}$ without significantly changing the $S_{0.5}$ in the presence of absence of ST. Inhibition of activity in the absence of a change in the affinity of the enzyme for substrate supports the suggestion that 2MeSATP inhibits particulate guanylyl cyclase by a non-competitive mechanism. These results are in close agreement with those described above utilizing manganese as the cation cofactor.

Previous studies have demonstrated that guanylyl cyclase in intestine is characterized by positively cooperative kinetics (Waldman et al., (1984) *J. Infect. Dis.*, 149, 83–89; Carr et al., (1989) *Int. J. Biochem.*, 21, 1211–1215). Indeed, analysis by the method of Lineweaver-Burke of the kinetics of intestinal guanylyl cyclase utilizing manganese as the cation cofactor demonstrated isotherms that were curvilinear suggesting catalytic sites which interacted in a positively cooperative fashion. Positive cooperativity was confirmed by analyzing these data by the method of Hill, which yielded coefficients greater than 1.0. Addition of 2MeSATP to enzyme incubations resulted in an alteration in the curvilinearity of the double reciprocal plots of particulate guanylyl cyclase activity from concave to convex. These data suggest a shift in the cooperativity of guanylyl cyclase activity from positive to negative, in a concentration-dependent fashion with respect to the adenine nucleotide analogue. This shift from positive to negative cooperativity was accomplished by a decrease in the Hill coefficient from 1.6 to 0.7 in a concentration-dependent fashion. ATP induced a similar shift in guanylyl cyclase kinetics from positive to negative cooperativity, with a reduction in the Hill coefficient to values less than 1.0. With magnesium as the cation cofactor, 1 mM 2MeSATP induced a consistent decrease in the Hill coefficient to about 1.0, in the presence and absence of SAT and double reciprocal plots yielded linear isotherms, suggesting a shift from positive to non-cooperative enzyme kinetics.

The data described herein suggests that GC-C is regulated by opposing adenine nucleotide-dependent pathways. Furthermore, selective agonists for each of these pathways have been identified. The inhibitory pathway is specifically activated by adenine nucleotide analogues substituted in the 2-position while the activating pathway is specifically potentiated by AMPS. The possibility that these nucleotides regulate guanylyl cyclase by interacting at a common site was explored by determining their efforts on enzyme activity when both were incorporated simultaneously in enzyme incubations. The potency of AMPS to potentiate ST-activation of guanylyl cyclase was not affected by 2ClATP at a concentration yielding half-maximum inhibition (Ki=0.3 mM). Indeed, the $K_a$ of AMPS was unchanged by incorporating 2ClATP in enzyme incubations. These data suggest 2ClATP does not interact with the site mediating AMPS activation. Similarly, the potency of 2ClATP to inhibit particulate guanylyl cyclase was not altered by maximally activating concentrations of AMPS (3 mM). Thus, the $K_i$ for 2ClATP was unchanged by incorporating AMPS in enzyme incubations. Furthermore, 21CATP inhibited >95% of the guanylyl cyclase activity in a concentration-dependent fashion in the presence of maximally activating concentrations of AMPS. These data support the suggestion that AMPS and 2ClATP do not compete for a common site regulating guanylyl cyclase. Rather, they suggest that the inhibitory and activating pathways are mediated by separate and independent sites.

DISCUSSION

Previous studies demonstrated that adenine nucleotides inhibited particulate guanylyl cyclase when manganese was utilized as the metal cofactor (Gazzano et al., (1991) *Biochim. Biophys. Acta*, 1077, 99–106; Gazzano et al., (1991) *Infect. Immun.*, 59, 1552–1557; Goraczniak et al., (1992) *Biochem. J.*, 282, 533–537). This inhibition was suggested to be mediated by substrate competition or a manganese-dependent ATP regulatory site. Studies described herein demonstrate that adenine nucleotides inhibit GC-C enzyme activity using manganese or magnesium as the cation factor. These data make it unlikely that inhibition is mediated by a specific manganese-dependent regulatory site. The present data suggest that adenine nucleotide-dependent inhibition is preferentially expressed when manganese is used as the substrate cofactor. Indeed, all ATP analogues tested inhibit guanylyl cyclase in the presence of manganese. Guanylyl cyclase exhibits maximum catalytic activity which is only the minimally responsive to peptide ligands when manganese serves as the cation cofactor. The mechanisms by which manganese regulates this enzyme and permits selective expression of the inhibitory pathway remain unclear. Manganese may fully activate the enzymes such that further increases by other activating agents cannot be observed, permitting only adenine nucleotide-dependent inhibition to be expressed. Alternatively, this cation may activate guanylyl cyclase by a mechanism similar to that mediating ATP-dependent potentiation of that enzyme when magnesium is used as the cofactor. In this model, GC-C would not be activated by adenine nucleotides when manganese is used since their mechanisms are convergent, and only inhibition of this enzyme by those nucleotides would be observed. Manganese may prevent the association of ATP with the kinase-like domain of GC-C allowing the expression of the inhibitory pathway, only (Vaandrager et al., (1993) *J. Biol. Chem.*, 268, 19598–19603). However, interaction of ATP with the putative activating site on the kinase-like domain is metal-independent, rendering this latter suggestion unlikely.

Data referred to herein suggest that inhibition of GC-C guanylyl cyclase activity by adenine nucleotide analogues is mediated by a non-competitive mechanism. Inhibition of manganese-stimulated guanylyl cyclase by 2MeSATP was concentration-dependent, decreasing the $V_{max}$ with only a small change in the $S_{0.5}$. Similarly, in the presence of magnesium, 2MeSATP decreased the $V_{max}$ of guanylyl cyclase with no effect on $S_{0.5}$. A decrease in the maximum velocity of the enzyme in the absence of an effect on substrate affinity was observed in the presence or absence of ST. The small change in $S_{0.5}$ observed in the presence of 2MeSATP using manganese as the cation cofactor is not likely to represent competitive inhibition of the enzyme since increasing the concentration of 2MeSATP 10-fold (from 0.1 mM to 1 mM) did not significantly increase the $S_{0.5}$ for substrate. Also, no change in the potency of 2MeSATP was observed when the GTP concentration was increased from 20 $\mu$M to mM, supporting the suggestion that 2MeSATP does not interact with the catalytic site of guanylyl cyclase. Taken together, these data suggest that adenine nucleotides inhibit guanylyl cyclase by a non-competitive mechanism.

Particulate guanylyl cyclase is preferentially inhibited by 2-substituted ATP analogues with the terminal phosphates playing a critical role. This is suggested by the failure of 2ClAdo to inhibit guanylyl cyclase while 2ClATp is the most potent inhibitor examined. Also, ATPγS and ADPβS were approximately equipotent as inhibitors of guanylyl cyclase in the presence of manganese while AMPS did not inhibit the enzyme. These data suggest that at least 2 terminal phosphate groups are required for inhibition of particulate guanylyl cyclase by adenine nucleotides.

Previous studies demonstrated that both ATP and ADP increased ANP-stimulated guanylyl cyclase activity in rat lung membranes while AMP had no effect (Chang et al., (1990) *Eur. J. Pharmacol.*, 189, 293–298). However, another report suggested that AMPS could activate basal guanylyl cyclase activity through AMP was without effect. The present study suggests that thiol-substitution of adenine nucleotides favors their interaction with the activating site of the ST-activated guanylyl cyclase from rat intestine. It also suggests that an AMP analogue can potentiate ligand-stimulated guanylyl cyclase activity since AMPS is a potent activator of guanylyl cyclase.

ATPγS is consistently more efficacious in activating particulate guanylyl cyclase than ATP although the reason for this is unclear. The effects of ATP and AMPS are not additive and therefore it is unlikely that the higher efficacy of ATPγS is due to the non-specific effect of a free thiol group. The difference in efficacy between ATPγS and ATP may reflect their different potencies for the two independent but opposing regulatory pathways. The efficacy of ATP in potentiating guanylyl cyclase activity may appear to be less than that of ATPγS because it is a more potent agonist of the inhibitory pathway than the thiol analogue. In this model, the inhibitory pathway regulates guanylyl cyclase at lower concentrations of ATP than ATPγS, resulting in inequivalent efficacies of ATP and ATPγS to activate this enzyme. If this hypothesis is correct, AMPS should be the most efficacious of all the nucleotides since it selectively activates guanylyl cyclase. However, AMPS may only serve as a partial agonist of the activating pathway since it lacks the terminal phosphates important for potentiation of enzyme activity (Vaandrager et al., (1993) *J. Biol. Chem.*, 268, 19598–19603; Chang et al., (1990) *Eur. J. Pharmacol.*, 189, 293–298).

Activation of guanylyl cyclase by adenine nucleotides has been suggested to reflect their direct interaction with the kinase-like domain of GC-C (Chinkers et al., (1991) *J. Biol. Chem.*, 266, 4088–4093; Duda et al., (1993) *FEBS Lett.*, 315:143–148; Vaandrager et al., (1993) *J. Biol. Chem.*, 268, 2174–2179; Vaandrager et al., (1993) *J. Biol. Chem.*, 268, 19598–19603). Adenine nucleotide interaction with this domain appears to stabilize the active conformation of GC-C and prevent desensitization of the enzyme in the presence of ST. In the present studies, inhibition and activation of guanylyl cyclase by adenine nucleotides appear to be mediated by separate non-interacting sites. The molecular mechanisms mediating inhibition of GC-C by these nucleotides remain to be elucidated. However, it is reasonable to suggest that inhibition of GC-C by these nucleotides remain to be elucidated. However, it is reasonable to suggest that inhibition may reflect stabilization of the less active conformation of GC-C. This hypothesis is currently being investigated.

The observations described herein, that adenine nucleotides inhibit particulate guanylyl cyclase, are similar to those reported previously that nucleotide analogues inhibit ANP-induced cGMP accumulation in intact FRTL-5 thyroid cells (Okajima et al., (1990) *J. Biol. Chem.*, 265, 21741–21748). Purine nucleotides were classified into three groups based on their mechanism of action. Group 2 agonists, including GTP, inhibited ANP-dependent accumulation through a mechanism involving activation of phospholipase C, calcium release, and activation of a calcium-dependent phosphodiesterase resulting in hydrolysis of cGMP. Group 3 agonists, including adenosine, inhibited guanylyl cyclase activity, probably through a pertussis toxin-sensitive G protein-mediated inactivation of ANP-stimulated guanylyl cyclase. Group 1 agonists, including ATP, were active through both mechanisms: initially ATP stimulated calcium release and then, following hydrolysis to adenosine, activated the G protein-coupled pathway. However, these mechanisms cannot underlie the observations obtained in the present studies. In these studies, cell-free membrane preparations were employed in the presence of a phosphodiesterase inhibitor, rendering calcium-dependent phosphodiesterase activation unlikely as the mechanism underlying guanylyl cyclase inhibition by adenine nucleotides. In addition, inclusion of EGTA in enzyme incubations had no effect on the ability of 2MeSATP or 2ClATP to inhibit particulate guanylyl cyclase. Also, in the earlier study, ATP was hydrolized to adenosine which inhibited guanylyl cyclase activity through a pertussis toxin-sensitive mechanism. In the present studies, AMPPCP and AMPCPP, hydrolysis resistant analogues of ATP (Burger et al., (1970) *J. Biol. Chem.*, 245, 6274–6280), were as potent as ATP in inhibiting particulate guanylyl cyclase.

The observations concerning the effects of adenine nucleotide inhibition on the kinetic characteristics of particulate guanylyl cyclase described in the present study are very similar to those described previously for sea urchin sperm particulate guanylyl cyclase (Garbers et al., (1974) *Biochemistry*, 13, 4166–4171). In those earlier studies, ATP inhibited guanylyl cyclase in the presence of manganese in a concentration-dependent fashion. Inhibition by ATP was associated with a concentration-dependent decrease in $V_{max}$ but only a small change in the $S_{0.5}$ of the enzyme. The authors suggested that the inhibitory effects of adenine nucleotides might be mediated by a separate allosteric inhibitory site. Also, a concentration-dependent decrease in the Hill coefficient was observed in the presence of ATP. This observation was attributed to saturation of an allosteric site with a subsequent linear dependence of enzyme activity on the substrate concentration reflected by the loss of positive cooperativity. The present studies suggest that adenine nucleotide-dependent inhibition may be more complex since the concentration-dependent inhibition of GC-C by ATP and its 2-substituted analogues resulted in a shift from positive to negative cooperativity. The present study confirms and extends hose earlier observations and supports the hypothesis that particulate guanylyl cyclase is regulated by opposing adenine nucleotide-dependent allosteric sites.

The shift in cooperativity of guanylyl cyclase induced by inhibitory adenine nucleotides could reflect the presence of multiple populations of that enzyme in intestinal membranes. Three particulate guanylyl cyclases have been identified by molecular cloning in mammalian intestines: GC-A, GC-B and GC-C (Schulz et al., (1990) *Cell*, 63, 941–948). GC-C is the receptor for ST and guanylin while GC-A and GC-B are receptors for natriuretic peptides, including ANP and CNP, respectively (Garbers, D. L., (1992) *Cell*, 71, 1–4). GC-C is specifically localized in mucosa cells while GC-A is localized in the lamina propria in the large intestine; GC-B was not detected in these studies (Li et al., (1993) *Am. J. Physiol.*, 265, G394–G402). ANP does not increase cGMP in rat intestinal mucosa cells, supporting the suggestion that these cells are devoid of GC-A (Vaandrager et al., (1992) *Gastroenterology*, 102, 1161–1169). The present studies employ intestinal membranes isolated from preparations commonly accepted to be enriched in mucosal, compared to submucosal, cells (Field et al., (1978) *Proc. Natl. Acad. Sci. USA*, 75, 2800–2804; Guerrant et al., (1980) *J. Infect. Dis.*, 142, 220–228). These membrane preparations did not exhibit guanylyl cyclase activation by 10 µM ANP or CNP, in the presence or absence of 1 mM ATP, conditions which induce maximum activation of GC-A and GC-B in other tissues (Koller et al., (1991) *Science*, 252, 120–123; Garbers, D. L., (1992) *Cell*, 71, 1–4). These data support the suggestion that GC-C is the only member of the receptor guanylyl cyclase family in intestinal membranes employed in the present studies.

Guanylyl cyclase C undergoes post-translations processing yielding multiple ST-binding proteins detected in crosslinking studies utilizing $^{125}$I-ST or by Western blot analysis (Vaandrager et al., (1993) *J. Biol. Chem.*, 268, 2174–2179; Vaandrager et al., (1993) *J. Biol. Chem.*, 268, 19598–19603; Ivens et al., (1990) *Infect. Immun.*, 58, 1817–1820; de Sauvage et al., (1993) *J. Biol. Chem.*, 267, 6479–6482; Cohen et al., (1993) *J. Cell. Physiol.*, 156, 138–144). Post-translational processing of GC-C appears to reflect heterogenicity of glycosylation and proteolysis. Processing has been observed in membranes examined from intestinal mucosal cells, intestinal cells grown in vitro, and mammalian cells expressing cloned rat or human GC-C. Thus, the shift in apparent cooperativity with associated changes in Hill coefficients induced by 2-substituted adenine nucleotides could reflect differences in their effects on different populations of GC-C in intestinal membranes. Guanylyl cyclase C is the predominant, if only, member of the particulate guanylyl cyclase family expressed by T84 and Caco 2 cells in vitro (Vaandrager et al., (1992) *Gastroenterology*, 102, 1161–1169). Of significance, these cells express GC-C predominantly as the native holoreceptor of 145- to 160 kDa (de Sauvage et al., (1993) *J. Biol. Chem.*, 267, 6479–6482; Cohen et al., (1993) *J. Cell. Physiol.*, 156, 138–144; Visweswariah et al., (1994) *Eur. J. Biochem.*, 219, 727–736). Therefore, these cells exhibit minimal post-translational processing of GC-C, 2MeSAZTP potently inhibited GC-C in membranes prepared from these cells. In addition, 2MeSATP resulted in a shift from positive to negative cooperativity of GC-C in membranes prepared from these cells, in close agreement with results obtained with native rat intestinal membranes. These data support the suggestion that adenine nucleotides inhibit GC-C by a non-competitive mechanism with a shift from positive to negative cooperativity.

The 2-substituted ATP analogues employed in the present studies are well-described agonists of extracellular $P_{2y}$ purinergic receptors. It is tempting to suggest a mechanism whereby activation of $P_{2y}$ receptors regulates ST receptor-coupled guanylyl cyclase in rat intestinal membranes. However, ADPβS is a potent ligand for $P_{2y}$ receptors but a poor inhibitor of guanylyl cyclase (Boyer et al., (1989) *J. Biol. Chem.*, 264, 884–890). Also, AMPCPP is a poor ligand for $P_{2y}$ receptors yet is approximately equipotent with ATP as an inhibitor of guanylyl cyclase in the presence of manganese. Thus, the known agonist potencies for $P_{2y}$ receptors of these nucleotides do not precisely overlap their inhibitory potencies for intestinal particulate guanylyl cyclase, suggesting that these receptors do not participate in this regulatory pathway. Whether $p^2$ purinergic receptors with unique agonists specificities mediate guanylyl cyclase inhibition is currently being examined.

The data referred to suggest that ATP activates opposing pathways regulating guanylyl cyclase in rat intestinal membranes. Interestingly, the Ka for ATP to potentiate guanylyl cyclase activation by ST is similar to the Ki for this nucleotide to inhibit that enzyme. Thus, it is unclear how ATP effectively regulates particulate guanylyl cyclase activity. While the kinase-like domain probably mediates ATP-dependent potentiation of guanylyl cyclase, the components mediating inhibition remain to be identified. One possible mechanism underlying the opposing effects of adenine nucleotides on guanylyl cyclase may involve asymmetric regulation of this enzyme across the plasma membrane. Adenine nucleotides in the cytoplasm may activate this enzyme by interacting with the kinase-like domain. In contrast, those nucleotides in the extracellular environment may interact with other sites, possibly a novel purinergic receptor, to inhibit particulate guanylyl cyclase. Tissue homogenization and membrane preparation may disrupt the normal barriers separating components of the inhibitory and activating pathways, permitting expression of both in the same cell-free preparation.

Alternatively, small differences in the Ka for ATP-dependent potentiation guanylyl cyclase and the Ki for ATP-dependent inhibition of this enzyme may be significant. In rat intestinal membranes, guanylyl cyclase exhibits a biphasic dose-response to ATP. Indeed, at concentrations above 1 mM, ATP inhibits guanylyl cyclase activity. Previously, this was attributed to competitive inhibition of guanylyl cyclase. However, the present studies suggest that inhibition of guanylyl cyclase at higher concentrations of adenine nucleotides reflects non-competitive regulation.

Thus, small changes in the intracellular concentrations of ATP might function to modulate the response of particulate guanylyl cyclase to extracellular ligands, such as ST and guanylin. In the presence of lower concentrations of ATP, guanylyl cyclase responses to ST would be amplified. In contrast, higher concentrations of ATP would antagonize the ability of guanylyl cyclase to be activated by ST.

In conclusion, adenine nucleotides activate opposing pathways regulating GC-C in rat intestinal mucosa membranes. The inhibitory pathway is specifically induced by 2-substituted ATP analogues while the activating pathway is selectively induced by AMPS. Also, inhibition by adenine nucleotides is selectively expressed when manganese is employed as the substrate cofactor. Inhibition of guanylyl cyclase by adenine nucleotidase appears to be mediated by a non-competitive mechanism. Activation and inhibition of particulate guanylyl cyclase by adenine nucleotides appear to be mediated by molecular mechanisms which are separate and independent.

Example 2

According to preferred embodiments of the invention, methods comprise the steps of: identifying an individual who is suffering from or susceptible to GC-C mediated diarrhea, particularly infectious diarrhea, and administering to such an individual, preferably by oral administration, an effective amount of a 2-substituted adenine nucleotide or 2-substituted adenine nucleoside compound, preferably a 2-substituted adenine nucleoside compound.

According to some preferred embodiments, 2-substituted adenine nucleotide or 2-substituted adenine nucleoside compounds administered according to the present invention treat prophylactically or therapeutically, an individual susceptible to or suffering from diarrhea, particularly infectious diarrhea, have the formula:

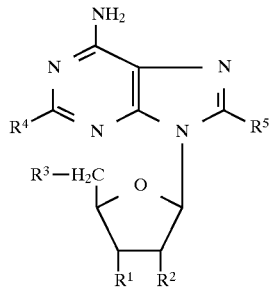

wherein the functional groups are selected as follows.

$R^1$ is OH; $R^2$ is OH; $R^3$ is OH; $R^4$ is Cl; and $R^5$ is H.
$R^1$ is OH; $R^2$ is OH; $R^3$ is $PO_4H_2$; $R^4$ is Cl; and $R^5$ is H.
$R^1$ is OH; $R^2$ is OH; $R^3$ is $P_2O_7H_3$; $R^4$ is Cl; and $R^5$ is H.
$R^1$ is OH; $R^2$ is OH; $R^3$ is $P_3O_{10}H_4$; $R^4$ is Cl; and $R^5$ is H.
$R^1$ is OH; $R^2$ is OH; $R^3$ is $P_4O_{13}H_7$; $R^4$ is Cl; and $R^5$ is H.
$R^1$ is OH; $R^2$ is OH; $R^3$ is OH: $R^4$ is methylthiol; and $R^5$ is H.
$R^1$ is OH; $R^2$ is OH; $R^3$ is $PO_4H_2$; $R^4$ is methylthiol; and $R^5$ is H.
$R^1$ is OH; $R^2$ is OH; $R^3$ is $P_2O_7H_3$; $R^4$ is methylthiol; and $R^5$ is H.
$R^1$ is OH; $R^2$ is OH; $R^3$ is $P_3O_{10}H_4$; $R^4$ is methylthiol; and $R^5$ is H.
$R^1$ is OH; $R^2$ is OH; $R^3$ is $P_4O_{13}H_7$; $R^4$ is methylthiol; and $R^5$ is H.
$R^1$ is OH; $R^2$ is OH; $R^3$ is OH; $R^4$ is Cl; and $R^5$ is Br.
$R^1$ is OH; $R^2$ is OH; $R^3$ is $PO_4H_2$; $R^4$ is Cl; and $R^5$ is Br.
$R^1$ is OH; $R^2$ is OH; $R^3$ is $P_2O_7H_3$; $R^4$ is Cl; and $R^5$ is Br.
$R^1$ is OH; $R^2$ is OH; $R^3$ is $P_3O_{10}H_4$; $R^4$ is Cl; and $R^5$ is Br.
$R^1$ is OH; $R^2$ is OH; $R^3$ is $P_4O_{13}H_7 R^4$ is Cl; and $R^5$ is Br.
$R^1$ is OH; $R^2$ is OH; $R^3$ is OH; $R^4$ is methylthiol; and $R^5$ is Br.
$R^1$ is OH; $R^2$ is OH; $R^3$ is $PO_4H_2$; $R^4$ is methylthiol; and $R^5$ is Br.
$R^1$ is OH; $R^2$ is OH; $R^3$ is $P_2O_7H_3$; $R^4$ is methylthiol; and $R^5$ is Br.
$R^1$ is OH; $R^2$ is OH; $R^3$ is $P_3O_{10}H_4$; $R^4$ is methylthiol; and $R^5$ is Br.
$R^1$ is OH; $R^2$ is OH; $R^3$ is $P_4O_{13}H_7$ [4] is methylthiol; and $R^5$ is Br.
$R^1$ is H; $R^2$ is OH; $R^3$ is OH; $R^4$ is Cl; and $R^5$ is H.
$R^1$ is H; $R^2$ is OH; $R^3$ is $PO_4H_2$; $R^4$ is Cl; and $R^5$ is H.
$R^1$ is H; $R^2$ is OH; $R^3$ is $P_2O_7H_3$; $R^4$ is Cl; and $R^5$ is H.
$R^1$ is H; $R^2$ is OH; $R^3$ is $P_3O_{10}H_4$; $R^4$ is Cl; and $R^5$ is H.
$R^1$ is H; $R^2$ is OH; $R^3$ is $P_4O_{13}H_7$; $R^4$ is Cl; and $R^5$ is H.
$R^1$ is H; $R^2$ is OH; $R^3$ is OH; $R^4$ is methylthiol; and $R^5$ is H.
$R^1$ is H; $R^2$ is OH; $R^3$ is $PO_4H_2$; $R^4$ is methylthiol; and $R^5$ is H.
$R^1$ is H; $R^2$ is OH; $R^3$ is $P_2O_7H_3$; $R^4$ is methylthiol; and $R^5$ is H.
$R^1$ is H; $R^2$ is OH; $R^3$ is $P_3O_{10}H_4$; $R^4$ is methylthiol; and $R^5$ is H.
$R^1$ is H; $R^2$ is OH; $R^3$ is $P_4O_{13}H_7$; $R^4$ is methylthiol; and $R^5$ is H.
$R^1$ is H; $R^2$ is OH; $R^3$ is OH; $R^4$ is Cl; and $R^5$ is Br.
$R^1$ is H; $R^2$ is OH; $R^3$ is $PO_4H_2$; $R^4$ is Cl; and $R^5$ is Br.
$R^1$ is H; $R^2$ is OH; $R^3$ is $P_2O_7H_3$; $R^4$ is Cl; and $R^5$ is Br.
$R^1$ is H; $R^2$ is OH; $R^3$ is $P_3O_{10}H_4$; $R^4$ is Cl; and $R^5$ is Br.
$R^1$ is H; $R^2$ is OH; $R^3$ is $P_4O_{13}H_7$; $R^4$ is Cl; and $R^5$ is Br.
$R^1$ is H; $R^2$ is OH; $R^3$ is OH: $R^4$ is methylthiol; and $R^5$ is Br.
$R^1$ is H; $R^2$ is OH; $R^3$ is $PO_4H_2$; $R^4$ is methylthiol; and $R^5$ is Br.
$R^1$ is H; $R^2$ is OH; $R^3$ is $P_2O_7H_3$; $R^4$ is methylthiol; and $R^5$ is Br.
$R^1$ is H; $R^2$ is OH; $R^3$ is $P_3O_{10}H_4$; $R^4$ is methylthiol; and $R^5$ is Br.
$R^1$ is H; $R^2$ is OH; $R^3$ is $P_4O_{13}H_7$; $R^4$ is methylthiol; and $R^5$ is Br.
$R^1$ is OH; $R^2$ is H; $R^3$ is OH; $R^4$ is Cl; and $R^5$ is H.
$R^1$ is OH; $R^2$ is H; $R^3$ is $PO_4H_2$; $R^4$ is Cl; and $R^5$ is H.
$R^1$ is OH; $R^2$ is H; $R^3$ is $P_2O_7H_3$; $R^4$ is Cl; and $R^5$ is H.
$R^1$ is OH; $R^2$ is H; $R^3$ is $P_3O_{10}H_4$; $R^4$ is Cl; and $R^5$ is H.
$R^1$ is OH; $R^2$ is H; $R^3$ is $P_4O_{13}H_7$; $R^4$ is Cl; and $R^5$ is H.
$R^1$ is OH; $R^2$ is H; $R^3$ is OH; $R^4$ is methylthiol; and $R^5$ is H.
$R^1$ is OH; $R^2$ is H; $R^3$ is $PO_4H_2$; $R^4$ is methylthiol; and $R^5$ is H.
$R^1$ is OH; $R^2$ is H; $R^3$ is $P_2O_7H_3$; $R^4$ is methylthiol; and $R^5$ is H.
$R^1$ is OH; $R^2$ is H; $R^3$ is $P_3O_{10}H_4$; $R^4$ is methylthiol; and $R^5$ is H.
$R^1$ is OH; $R^2$ is H; $R^3$ is $P_4O_{13}H_7$; $R^4$ is methylthiol; and $R^5$ is H.

$R^1$ is OH; $R^2$ is H; $R^3$ is OH; $R^4$ is Cl; and $R^5$ is Br.
$R^1$ is OH; $R^2$ is H; $R^3$ is $PO_4H_2$; $R^4$ is Cl; and $R^5$ is Br.
$R^1$ is OH; $R^2$ is H; $R^3$ is $P_2O_7H_3$; $R^4$ is Cl; and $R^5$ is Br.
$R^1$ is OH; $R^2$ is H; $R^3$ is $P_3O_{10}H_4$; $R^4$ is Cl; and $R^5$ is Br.
$R^1$ is OH; $R^2$ is H; $R^3$ is $P_4O_{13}H_7 R^4$ is Cl; and $R^5$ is Br.
$R^1$ is OH; $R^2$ is H; $R^3$ is OH; $R^4$ is methylthiol; and $R^5$ is Br.
$R^1$ is OH; $R^2$ is H; $R^3$ is $PO_4H_2$; $R^4$ is methylthiol; and $R^5$ is Br.
$R^1$ is OH; $R^2$ is H; $R^3$ is $P_2O_7H_3$; $R^4$ is methylthiol; and $R^5$ is Br.
$R^1$ is OH; $R^2$ is H; $R^3$ is $P_3O_{10}H_4$; $R^4$ is methylthiol; and $R^5$ is Br.
$R^1$ is OH; $R^2$ is H; $R^3$ is $P_4O_{13}H_7$; $R^4$ is methylthiol; and $R^5$ is Br.
$R^1$ is H; $R^2$ is H; $R^3$ is OH; $R^4$ is Cl; and $R^5$ is H.
$R^1$ is H; $R^2$ is H; $R^3$ is $PO_4H_2$; $R^4$ is Cl; and $R^5$ is H.
$R^1$ is H; $R^2$ is H; $R^3$ is $P_2O_7H_3$; $R^4$ is Cl; and $R^5$ is H.
$R^1$ is H; $R^2$ is H; $R^3$ is $P_3O_{10}H_4$; $R^4$ is Cl; and $R^5$ is H.
$R^1$ is H; $R^2$ is H; $R^3$ is $P_4O_1\_H_7$; $R^4$ is is Cl; and $R^5$ is H.
$R^1$ is H; $R^2$ is H; $R^3$ is OH; $R^4$ is methylthio; and $R^5$
$R^1$ is H; $R^2$ is H; $R^3$ is OH; $R^4$ is methylthiol; and $R^5$ is H.
$R^1$ is H; $R^2$ is H; $R^3$ is $PO_4H_2$; $R^4$ is methylthiol; and $R^5$ is H.
$R^1$ is H; $R^2$ is H; $R^3$ is $P_2O_7H_3$; $R^4$ is methylthiol; and $R^5$ is H.
$R^1$ is H; $R^2$ is H; $R^3$ is $P_3O_{10}H_4$; $R^4$ is methylthiol; and $R^5$ H.
$R^1$ is H; $R^2$ is H; $R^3$ is $P_4O_{13}H_7 R^4$ is methylthiol; and $R^5$ is H.
$R^1$ is H; $R^2$ is H; $R^3$ is OH; $R^4$ is Cl; and $R^5$ is Br.
$R^1$ is H; $R^2$ is H; $R^3$ is $PO_4H_2$; $R^4$ is Cl; and $R^5$ is Br.
$R^1$ is H; $R^2$ is H; $R^3$ is $P_2O_7H_3$; $R^4$ is Cl; and $R^5$ is Br.
$R^1$ is H; $R^2$ is H; $R^3$ is $P_3O_{10}H_4$; $R^4$ is Cl; and $R^5$ is Br.
$R^1$ is H; $R^2$ is H; $R^3$ is $P_4O_{13}H_7$; $R^4$ is Cl; and $R^5$ is Br.
$R^1$ is H; $R^2$ is H; $R^3$ is OH; $R^4$ is methylthiol; and $R^5$ is Br.
$R^1$ is H; $R^2$ is H; $R^3$ is $PO_4H_2$; $R^4$ is methylthiol; and $R^5$ is Br.
$R^1$ is H; $R^2$ is H; $R^3$ is $P_2O_7H_3$; $R^4$ is methylthiol; and $R^5$ is Br.
$R^1$ is H; $R^2$ is H; $R^3$ is $P_3O_{10}H_4$; $R^4$ is methylthiol; and $R^5$ is Br.
$R^1$ is H; $R^2$ is H; $R^3$ is $P_4O_{13}H_7$; $R^4$ is methylthiol; and $R^5$ is Br.

We claim:
1. A method of treating an individual who has enterotoxigenic diarrhea comprising the steps of:

identifying said individual as an individual who has enterotoxigenic diarrhea; and
administering to said individual, an effective amount of a 2-substituted adenine nucleoside having the formula:

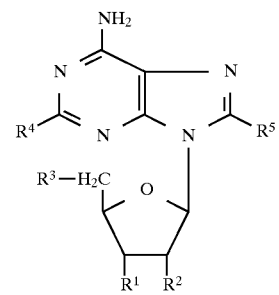

wherein:
$R^1$ is OH or H;
$R^2$ is OH or H;
$R^3$ is OH;
$R^4$ is halogen, $C_1$–$C_4$ alkyl, $C_1$–$C_4$ alkoxy, or $C_1$–$C_4$ alkylthiol; and,
$R^5$ is H, Cl or Br;
or a pharmaceutically acceptable salt thereof.

2. The method of claim 1 wherein said 2-substituted adenine nucleoside is administered orally.

3. The method of claim 1 wherein said 2-substituted adenine nucleoside is administered orally as an enteric coated composition.

4. The method of claim 1 wherein $R^1$ is OH.

5. The method of claim 1 wherein $R^2$ is OH.

6. The method of claim 1 wherein $R^1$ is H.

7. The method of claim 1 wherein $R^2$ is H.

8. The method of claim 1 wherein $R^1$ is OH and $R^2$ is OH.

9. The method of claim 1 wherein $R^1$ is OH and $R^2$ is H.

10. The method of claim 1 wherein $R^1$ is H and $R^2$ is OH.

11. The method of claim 1 wherein $R^4$ is F, Cl, Br, I or At.

12. The method of claim 1 wherein $R^4$ is Cl.

13. The method of claim 1 wherein $R^4$ is a methyl, ethyl, propyl or butyl.

14. The method of claim 1 wherein $R^4$ is a methyoxy, ethoxy, propyloxy or butyloxy.

15. The method of claim 1 wherein $R^4$ is methylthiol, ethylthiol, propylthiol or butylthiol.

16. The method of claim 1 wherein $R^4$ is methylthiol.

17. The method of claim 1 wherein $R^5$ is H.

18. The method of claim 1 wherein $R^5$ is Br.

19. The method of claim 1 wherein: Ris OH; $R^2$ is OH; $R^3$ is OH; $R^4$ is Cl, $C_1$–$C_2$ alkoxyl, $C_1$–$C_2$ alkylthiol; and, $R^5$ is H or Br.

20. The method of claim 1 wherein: $R^1$ is OH; $R^2$ is OH; $R^3$ is OH; $R^4$ is Cl, methyl, methoxy or methylthiol; and, $R^5$ is H or Br.

21. The method of claim 1 wherein: $R^1$ is OH; $R^2$ is OH; $R^3$ is OH; $R^4$ is Cl; and $R^5$ is H.

22. The method of claim 1 wherein: $R^1$ is OH; $R^2$ is OH; $R^3$ is OH; $R^4$ is methylthiol; and $R^5$ is H.

23. A method of preventing enterotoxigenic diarrhea in an individual who is at risk of contracting enterotoxigenic diarrhea comprising the steps of:

a) identifying said individual as being at risk of contracting enterotoxigenic diarrhea; and
b) administering to said individual, a prophylactically effective amount of a 2-substituted adenine nucleoside having the formula:

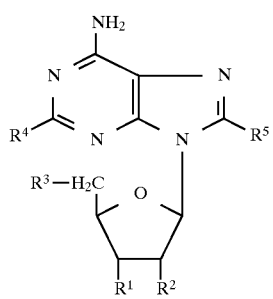

wherein:
R¹ is OH or H;
R² is OH or H;
R³ is OH;
R⁴ is halogen, $C_1$–$C_4$ alkyl, $C_1$–$C_4$ alkoxyl, or $C_1$–$C_4$ alkylthiol; and,
R⁵ is H, Cl or Br;
or a pharmaceutically acceptable salt thereof.

24. The method of claim 23 wherein said individual who is identified as being at risk of contracting enterotoxigenic diarrhea is identified as an individual who is traveling to a location where said individual is at an elevated risk of being exposed to a pathogen responsible for enterotoxigenic diarrhea.

25. The method of claim 23 wherein said 2-substituted adenine nucleoside is administered orally.

26. The method of claim 23 wherein said 2-substituted adenine nucleoside is administered orally as an enteric coated composition.

27. The method of claim 23 wherein $R^1$ is OH.
28. The method of claim 23 wherein $R^2$ is OH.
29. The method of claim 23 wherein $R^1$ is H.
30. The method of claim 23 wherein $R^2$ is H.
31. The method of claim 23 wherein $R^1$ is OH and $R^2$ is OH.
32. The method of claim 23 wherein $R^1$ is OH and $R^2$ is H.
33. The method of claim 23 wherein $R^1$ is H and $R^2$ is OH.
34. The method of claim 23 wherein $R^4$ is F, Cl, Br, I or At.
35. The method of claim 23 wherein $R^4$ is Cl.
36. The method of claim 23 wherein $R^4$ is a methyl, ethyl, propyl or butyl.
37. The method of claim 23 wherein $R^4$ is a methoxy, ethoxy, propyloxy or butyloxy.
38. The method of claim 23 wherein $R^4$ is methylthiol, ethylthiol, propylthiol or butylthiol.
39. The method of claim 23 wherein $R^4$ is methylthiol.
40. The method of claim 23 wherein $R^5$ is H.
41. The method of claim 23 wherein $R^5$ is Br.
42. The method of claim 23 wherein: $R^1$ is OH; $R^2$ is OH; $R^3$ is OH; $R^4$ is Cl, $C_1$–$C_2$ alkyl, $C_1$–$C_2$ alkoxy, or $C_1$–$C_2$ alkylthiol; and $R^5$ is H or Br.
43. The method of claim 23 wherein: $R^1$ is OH; $R^2$ is OH; $R^3$ is OH; $R^4$ is Cl, methyl, methoxy or methylthiol; and $R^5$ is H or Br.
44. The method of claim 23 wherein: $R^1$ is OH; $R^2$ is OH; $R^3$ is OH; $R^4$ is Cl; and $R^5$ H.
45. The method of claim 23 wherein: $R^1$ is OH; $R^2$ is OH; $R^3$ is OH; $R^4$ is methylthiol; and $R^5$ is H.

* * * * *

UNITED STATES PATENT AND TRADEMARK OFFICE
CERTIFICATE OF CORRECTION

PATENT NO. : 5,817,641
DATED : October 6 1998
INVENTOR(S) : Scott A. Waldman et al It is certified that error appears in the above-identified patent and that said Letters Patent is hereby corrected as shown below:

Claim 19 should read as follows:

--19. The method of claim 1 wherein: $R^1$ is OH; $R^2$ is OH; $R^3$ is OH; $R^4$ is $C_1$, $C_1$-$C_2$ alkyl, $C_1$-$C_2$ alkoxyl, or $C_1$-$C_2$ alkylthiol; and $R^5$ is H or Br.--

Signed and Sealed this

Eleventh Day of May, 1999

*Attest:*

Q. TODD DICKINSON

*Attesting Officer*       Acting Commissioner of Patents and Trademarks